United States Patent [19]

Kane

[11] Patent Number: 5,031,775
[45] Date of Patent: Jul. 16, 1991

[54] MEDICAL INSTRUMENT HOLDER

[75] Inventor: Lawrence M. Kane, Roseville, Minn.

[73] Assignee: Angeion Corporation, Plymouth, Minn.

[21] Appl. No.: 480,001

[22] Filed: Feb. 14, 1990

[51] Int. Cl.$^5$ ............................................. B65D 69/00
[52] U.S. Cl. ........................... 206/571; 128/DIG. 26; 206/364; 206/370; 206/438; 604/179
[58] Field of Search ............... 206/363, 369, 370, 438, 206/439, 570–572; 604/119, 169, 51, 53, 179, 180; 248/68.1, 74.2, 316.7; 128/DIG. 26; 24/DIG. 11

[56] References Cited

U.S. PATENT DOCUMENTS

| | | | |
|---|---|---|---|
| 2,261,213 | 11/1941 | Bierman | 604/179 |
| 2,322,753 | 6/1943 | Thomas | 248/68.1 X |
| 2,452,643 | 11/1948 | Fields | 206/364 |
| 2,831,487 | 4/1958 | Tafilaw | 128/DIG. 26 |
| 3,013,656 | 12/1961 | Murphy, Jr. | 206/370 X |
| 3,210,816 | 10/1965 | Clemons | 128/DIG. 26 |
| 3,861,395 | 1/1975 | Taniguchi | 206/364 X |
| 4,029,103 | 6/1977 | McConnell | 604/179 X |
| 4,164,943 | 8/1979 | Hill et al. | 128/DIG. 26 |
| 4,216,860 | 8/1980 | Heimann | 206/370 |
| 4,262,800 | 4/1981 | Nethercutt | 206/364 |
| 4,266,669 | 5/1981 | Watson | 206/370 X |
| 4,332,322 | 6/1987 | Jaeschke et al. | 206/364 |
| 4,419,094 | 12/1983 | Patel | 128/DIG. 26 |
| 4,545,783 | 10/1985 | Vaughan | 206/438 X |
| 4,573,576 | 3/1986 | Krol | 206/438 X |
| 4,823,167 | 4/1989 | Manska et al. | 206/364 X |
| 4,863,016 | 9/1989 | Fong et al. | 206/439 X |
| 4,898,586 | 2/1990 | McDonough | 206/364 X |

Primary Examiner—Bryon P. Gehman
Attorney, Agent, or Firm—Hugh D. Jaeger

[57] ABSTRACT

A medical instrument holder, also referred to as a packaging clip, for supporting disposable medical instruments for cardiology and cardiovascular procedures. The medical instrument holder is a one-piece polymer molded member, including a frictionally engaged tube, in the holder for supporting a guidewire. The holder also includes at least one slot for a medical instrument in the form of a partial circle to prevent axial movement, and preferably two slots for frictionally engaging a dilator and a hemostasis valve introducer, or a needle and a tear-away sheath/dilator assembly. The holder can also include at least one hole for receiving a medical instrument. The one-piece molded member, including the frictionally engaged guidewire tube, provides for disposable packaging in a Tyvek/Mylar pouch which lends itself conveniently to ETO sterilization. The holder, along with its instruments, is compact and minimal in length because the guidewire is looped about itself. The holder is ergonomically designed with an individual's dexterity in mind for convenient handling of the disposable medical instruments supported in the holder.

11 Claims, 5 Drawing Sheets

MEDICAL INSTRUMENT HOLDER

BACKGROUND OF THE INVENTION

1. Field of the Invention

The present invention is a medical instrument holder, also referred to as a packaging clip, and more particularly, pertains to a medical instrument holder for a stopcock, hemostasis valve introducer with a connecting tube, a dilator, and a guidewire with an introducer; alternatively, a tear-away sheath/dilator assembly, needle and guidewire; or alternatively, a sheath, syringe, dilator, guidewire and Seldinger needle.

2. Description of the Prior Art

Prior art medical instrument holders have been long, slim plastic trays, especially for instrumentation, including guidewires, hemostasis valve introducers, dilator tear-away sheaths, or needles. The long packages have been difficult to sterilize, to store, to dispose of, and to handle.

The present invention overcomes the disadvantages of the prior art by providing a medical instrument holder which provides for a guidewire to loop about itself and provides a package of significant shortness, as well as compactness for storage.

SUMMARY OF THE INVENTION

The general purpose of the present invention is to provide a medical instrument holder, also referred to as a packaging clip, for holding disposable medical instruments utilized in cardiology and cardiovascular procedures, such as angiography or pacemaker lead implantation.

According to one embodiment of the present invention, there is provided a medical instrument holder, including a polymer body member with an outwardly extending stopcock arm with a stopcock pin on the one end. A guidewire tube extends between two guidewire slots in the form of a partial circle to prevent axial movement in the back side of the support. Two slots or holes support a dilator and a tube-like device which is either a hemostasis valve introducer or tear-away sheath introducer. Additionally, a Seldinger needle and syringe can also be mounted in or about the clip.

Significant aspects and features of the present invention include a medical instrument holder, also referred to as a packaging clip, which lends itself to compact, sterilizable packaging, and further supports disposable medical instruments in an ergonomically designed structure which provides for easy manual dexterity of removal.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENT

Figure 1:
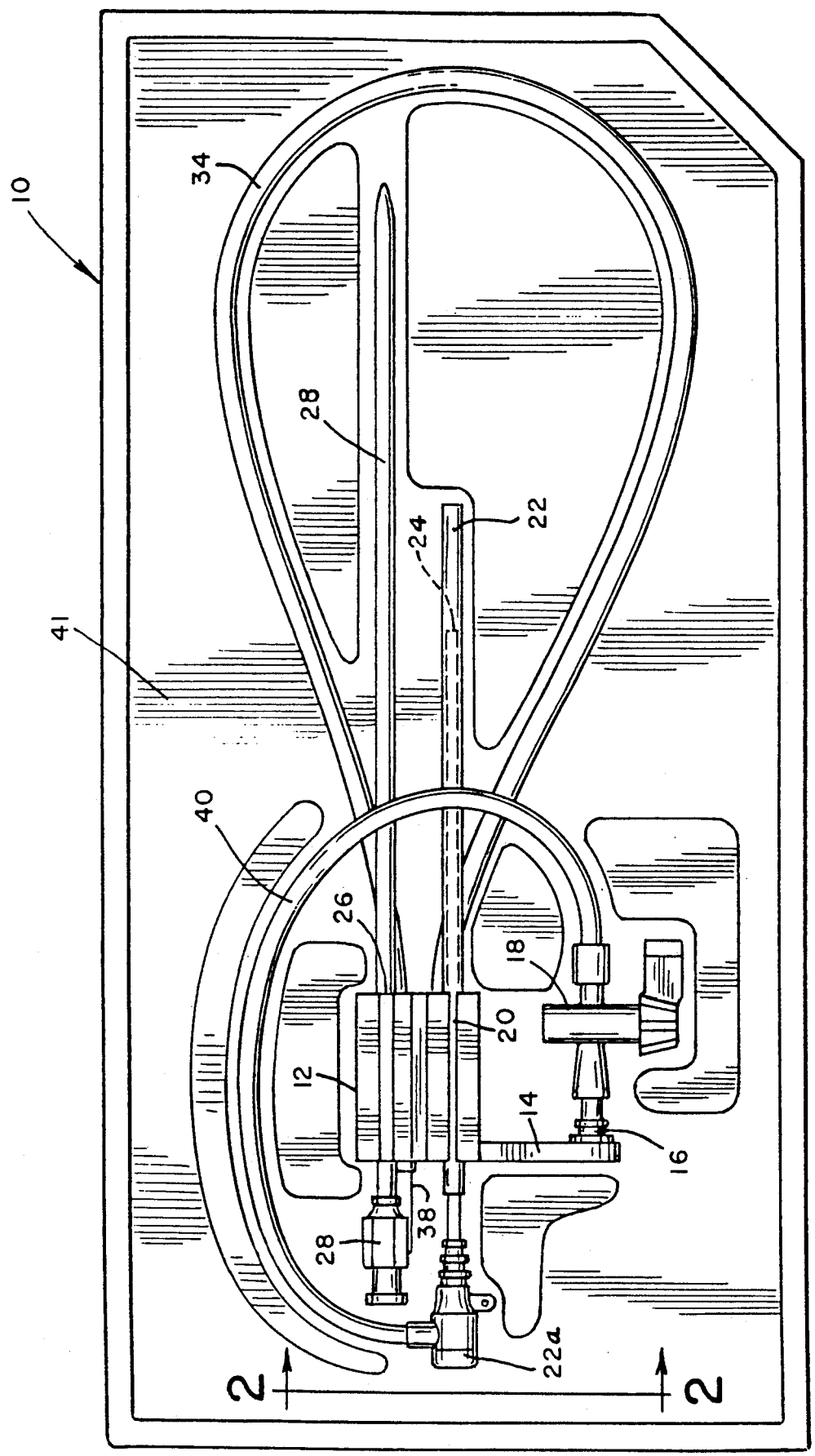
FIG. 1 illustrates a front view of a medical instrument holder including a stopcock, a hemostasis valve introducer with a connecting tube to the stopcock, a dilator, and a guidewire tube, the present invention.
Figure 2:
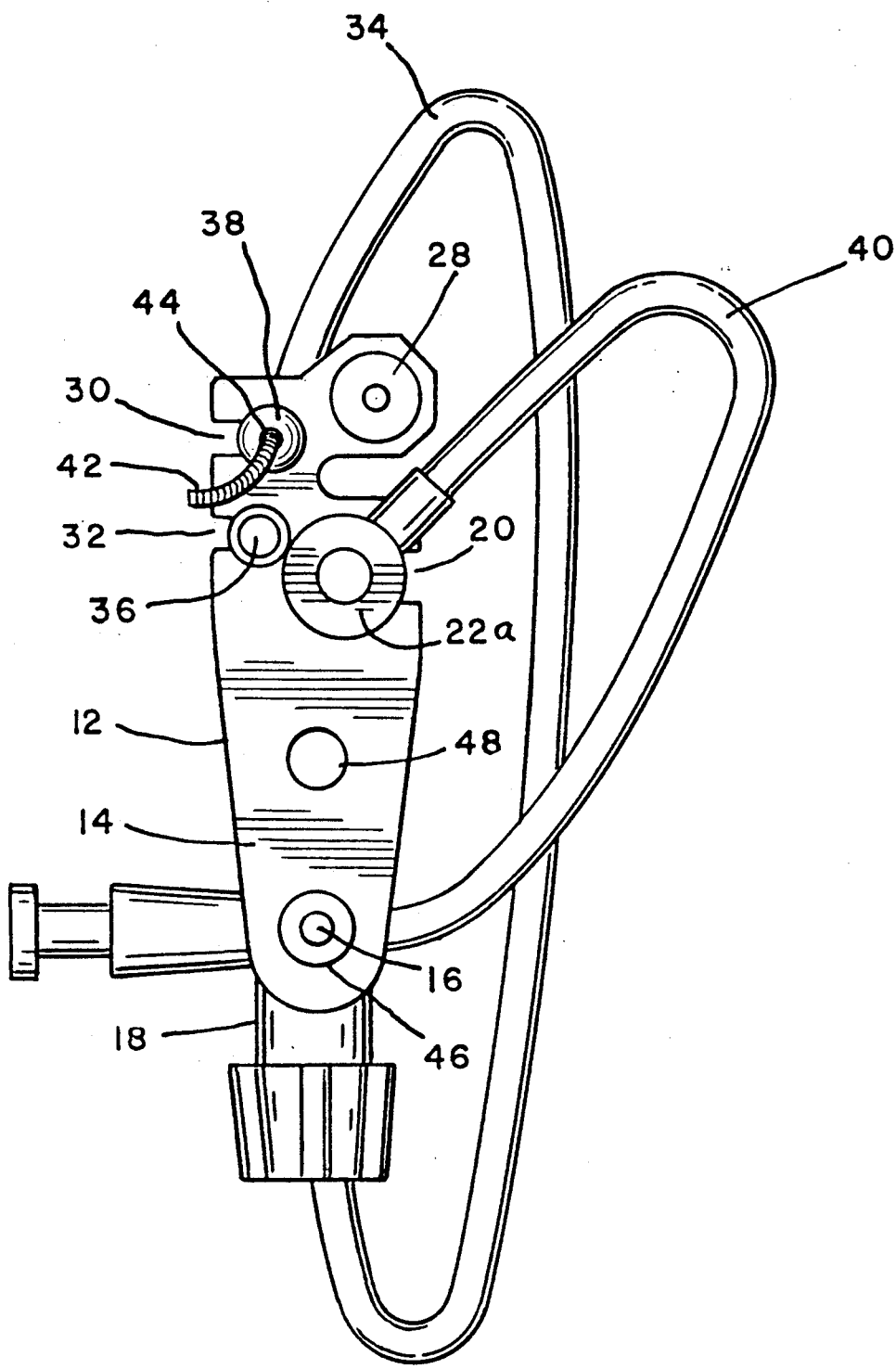
FIG. 2 illustrates a sectional view taken along lines 2—2 of FIG. 1.

FIG. 1, the present invention illustrates a front view of a medical instrument holder 10, also referred to as a packaging clip. The medical instrument holder 10 includes a body member 12 which can be injection molded, machine molded or cast of any suitable material, such as a polymer material. The body member 12 includes an integral outwardly extending stopcock arm 14 with a stopcock pin 16 extending perpendicular from the stopcock arm 14 for engaging to and supporting a stopcock assembly 18 on one side thereof. In this example, for purposes of illustration only and not to be construed as limiting of the present invention, there is at least one horizontally aligned slot 20 in the form of a partial circle to prevent axial movement and to support a tube 22 which contains a hemostasis valve introducer 24 concentrically located within. At least one horizontally aligned hole 26 accommodates a dilator 28. On the back side of the body member 12 as illustrated in FIG. 2, are two slots 30 and 32 in the form of a partial circle to prevent axial movement and for supporting a preferably continuous guidewire tube 34, including an open end 36, a guidewire support 38 and a slot 30 in the guidewire support 38 at about a top edge of the instrument holder 10. A tube 40 connects between the stopcock assembly 18 and an end 22a of the hemostasis valve introducer 24 and is configured to prevent movement of the hemostasis valve introducer 24 out of its protective tube 22. The holder and components attached thereto can be housed in a Tyvek/Mylar package 41. The slot(s) and hole(s) can be arranged as dictated by the particular instruments.

FIG. 2 illustrates an end view taken along line 2—2 of FIG. 1 where all numerals correspond to those elements previously described. The physical location of the components is denoted in this illustration in detail. A guidewire 42 is positioned in hole 44 of the guidewire tube 22. A hole 46 accommodates the stopcock pin 16. Another hole 48 is located the hole 46 for accommodation of another luer fitting or tip of a syringe as described later in FIG. 3.

Figure 3:
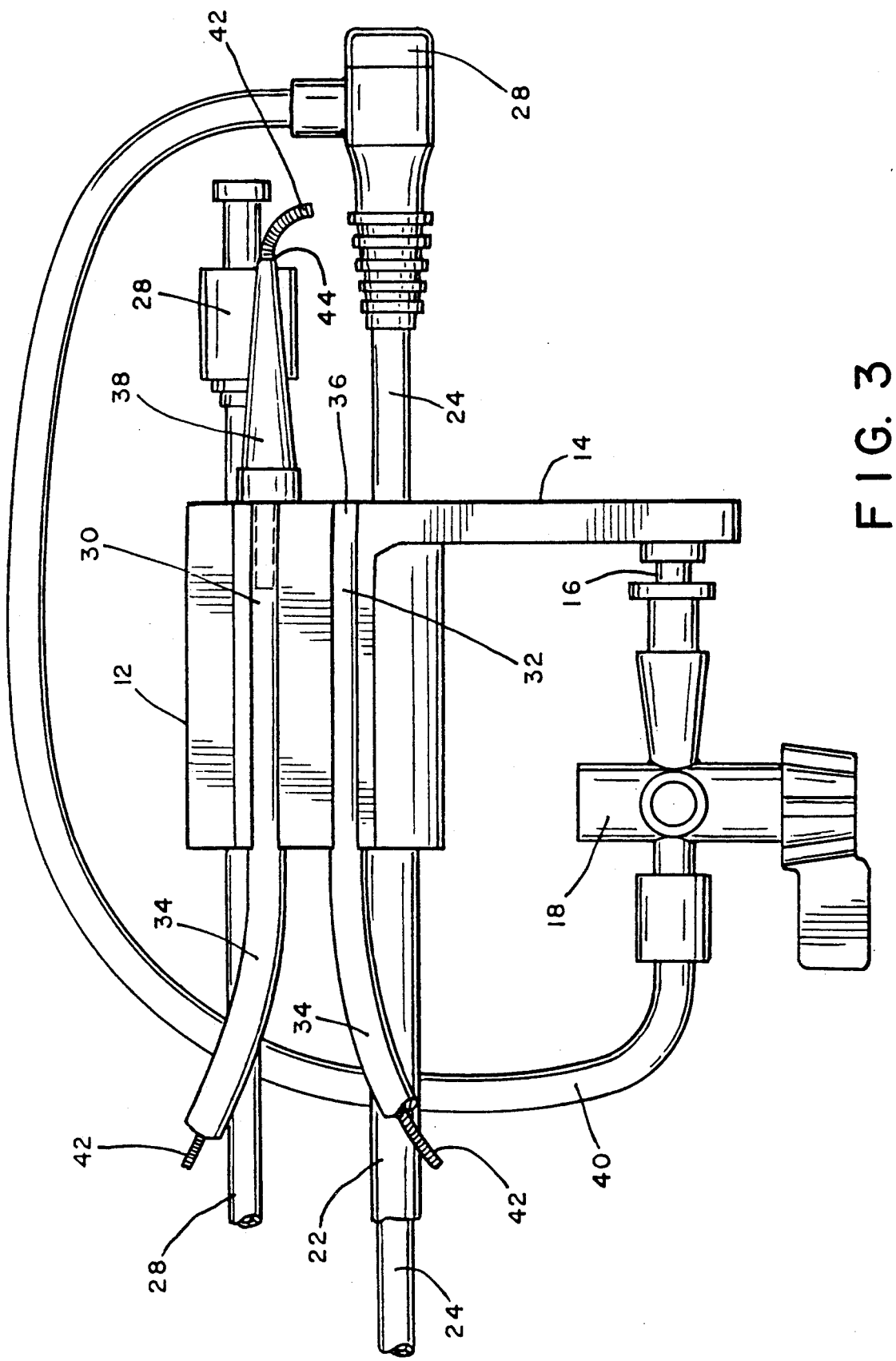
FIG. 3 illustrates an enlarged back view of FIG. 1.

FIG. 3 illustrates an enlarged back view of FIG. 1 where all numerals correspond to those elements previously described. Illustrated in particular are slots 30 and 32 in the form of a partial circle to prevent axial movement for accommodation and grasping of the guidewire tube 34. The guidewire support 38 extends into the inner radius of the guidewire tube 34.

Figure 4:
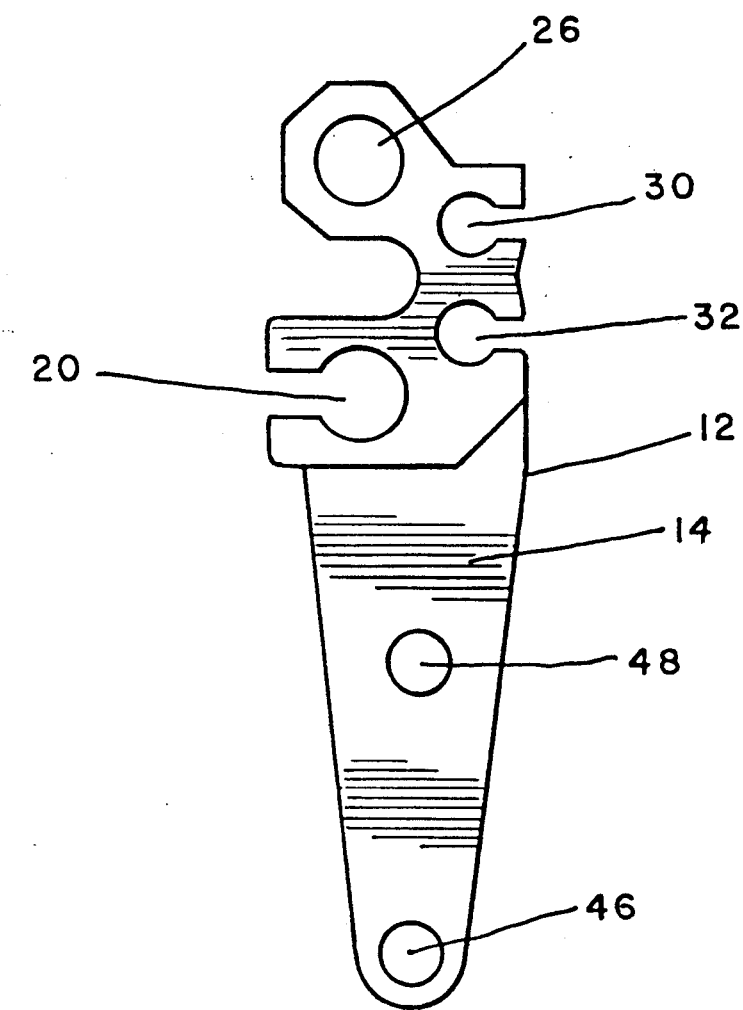
FIG. 4 illustrates a plane view of the body member.

FIG. 4 illustrates a plan view of the body member 12 where all numerals correspond to those elements previously described. Attached devices are removed therefrom for brevity and clarity of illustration. Illustrated in particular are the slots 20, 30 and 32 each of which is in the form of a partial circle in which the tubing is grasped.

MODE OF OPERATION

The disposable medical instruments, including the hemostasis valve introducer 24 and dilator 28 are engaged into the hole 26 and the partial circle slot 20 of the medical instrument holder 10, as well as the tube 22 which is held in slots 30 and 32 by way of example and for purposes of illustration only and not to be construed as limiting of the present invention. The medical instrument holder 10 with the instruments can then be placed into a Tyvek/Mylar pouch 41 as a unit package as illustrated in FIG. for later sterilization. The package 41 can be opened at the end with the tube 22, and the tube 22 is pulled from the package 41, removing all contents from the package 41. The three-way stopcock assembly 18 is removed from the stopcock pin 16, and the dilator 28 and tube 22 removed from the package 41. The guidewire 42 is then removed. For the tear-away sheath configuration, the needle 56 and tear-away sheath/dilator assembly 58 and 60 are removed, and then the guidewire 42 is removed from its medical instrument holder 10.

DESCRIPTION OF THE ALTERNATIVE EMBODIMENT

Figure 5:
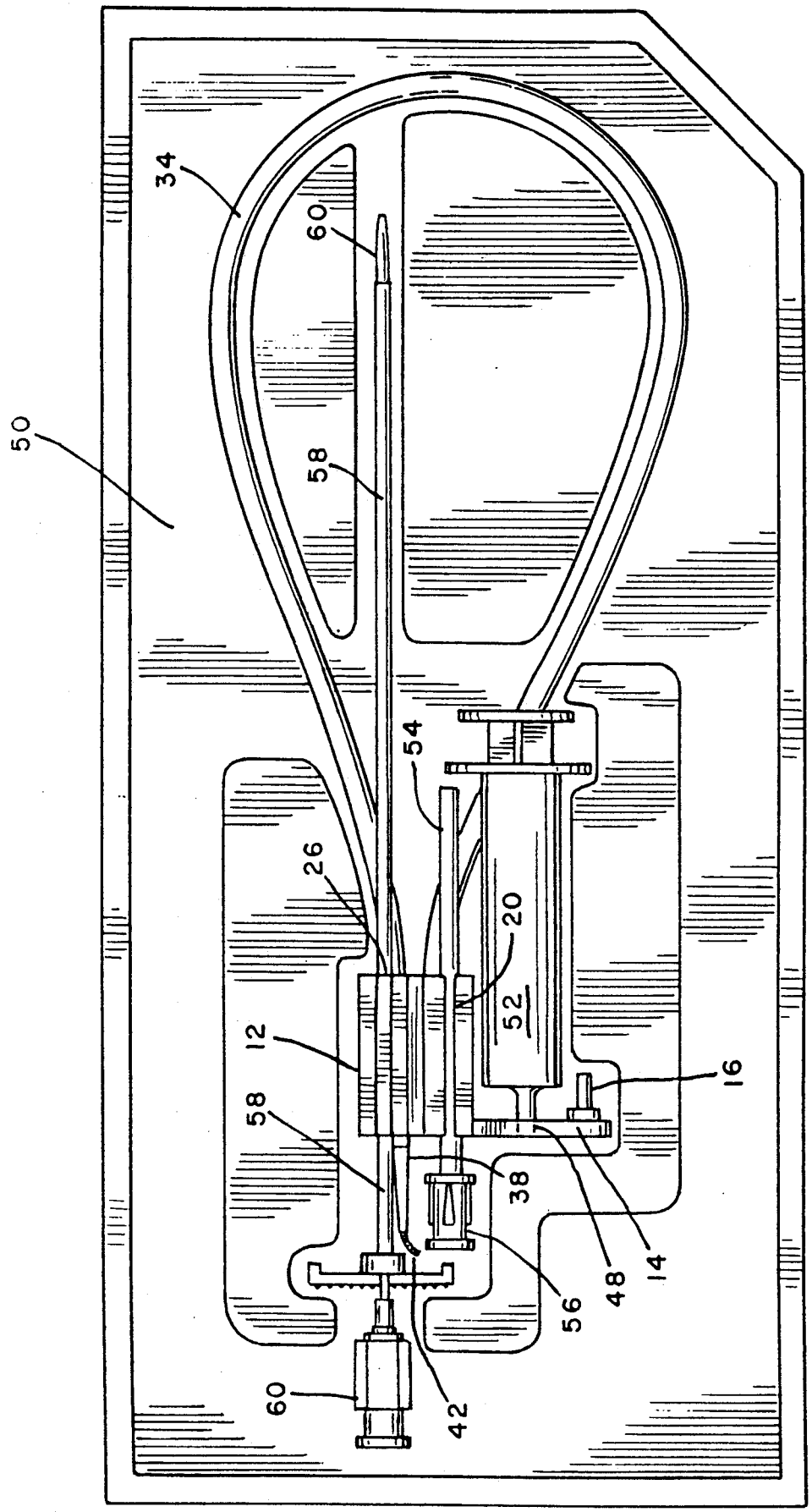
FIG. 5 illustrates a front view of an alternative embodiment of a medical instrument holder with a syringe, a needle and sheath, a dilator and tear-away sheath, and a guidewire tube.

FIG. 5 illustrates a plan view of an alternative embodiment of a medical instrument holder 10 in a Tyvek/Mylar pouch 50 where a syringe 52 is engaged by hole 48 in the medical instrument holder 10. A needle sheath 54, with a needle 56, engages therein and is held in slot 20. A tear-away sheath 58 with a dilator 60 contained therein is held in hole 26.

Various modifications can be made to the present invention without departing from the apparent scope hereof. The teachings of the present invention can be expanded to support desired disposable medical instruments.

I claim:

1. Medical instrument holder for holding a plurality of instruments for a cardiology procedure comprising:
  a. a molded body member;
  b. a stopcock arm connected to said body member and including a stopcock pin connected thereto;
  c. at least one slot in said body member in the form of a partial circle in cross-section in said body member for frictionally engaging at least one instrument; and
  d. a guidewire tube connected to said body member.

2. Medical instrument holder of claim 1 including a tear-away sheath in said at least one slot.

3. Medical instrument holder of claim 1 comprising a second slot in said body member.

4. Medical instrument holder of claim 3 including a hemostasis valve introducer in said second slot.

5. Medical instrument holder of claim 1 including a hole in said body member.

6. Medical instrument holder of claim 5 including a tear-away sheath in said hole.

7. Medical instrument holder of claim 6 including a tube supporting said tear-away sheath.

8. Medical instrument holder comprising:
  a. a molded body member including an integral stopcock arm and including a stopcock pin at an end of said arm;
  b. at least one front slot in said molded body member in the form of a partial circle in cross-section and located on a front face of said molded body member;
  c. at least one hole in said molded body member for engaging an instrument or an instrument holder; and,
  d. at least two back slots, each in the form of a partial circle in cross-section located on a back face of said molded body member and including a tube engaged in said back slots for receiving a guidewire.

9. Medical instrument holder of claim 8 including a tear-away sheath in said at least one hole.

10. Medical instrument holder of claim 8 including a hemostasis valve introducer in said at least one front slot.

11. Disposable medical instrument holder comprising:
  a. a body including a plurality of holes and slots;
  b. a guidewire tube engaged in one of said slots;
  a syringe in one of said holes;
  d. a sheath and a needle in one of said slots; and,
  e. a sheath and a dilator in one of said slots.

* * * * *